(12) United States Patent
Eng et al.

(10) Patent No.: US 8,647,653 B2
(45) Date of Patent: Feb. 11, 2014

(54) WATER CONTAINING POWDER COMPOSITION

(75) Inventors: Jennifer C. Eng, South Hampton, NJ (US); Matthew Romaine, Franklin Park, NJ (US); Christopher Proulx, Piscataway, NJ (US)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/519,515

(22) PCT Filed: Nov. 26, 2010

(86) PCT No.: PCT/EP2010/068324
§ 371 (c)(1),
(2), (4) Date: Aug. 9, 2012

(87) PCT Pub. No.: WO2011/076518
PCT Pub. Date: Jun. 30, 2011

(65) Prior Publication Data
US 2013/0022656 A1    Jan. 24, 2013

Related U.S. Application Data

(60) Provisional application No. 61/290,205, filed on Dec. 26, 2009.

(51) Int. Cl.
*A61K 8/11* (2006.01)
*A61K 8/25* (2006.01)
*A61K 9/50* (2006.01)

(52) U.S. Cl.
USPC ............ 424/417; 424/401; 424/490; 424/724

(58) Field of Classification Search
None
See application file for complete search history.

(56) References Cited

U.S. PATENT DOCUMENTS

| | | | |
|---|---|---|---|
| 2006/0153764 A1 | 7/2006 | Schumacher et al. | |
| 2007/0154426 A1 | 7/2007 | Hansen et al. | |
| 2007/0218024 A1* | 9/2007 | Zamyatin et al. | 424/63 |
| 2009/0047225 A1 | 2/2009 | Hasenzahl et al. | |
| 2009/0298952 A1* | 12/2009 | Brimmer et al. | 514/770 |
| 2012/0315312 A1* | 12/2012 | Riedemann et al. | 424/401 |

FOREIGN PATENT DOCUMENTS

| | | |
|---|---|---|
| CN | 1382034 A | 11/2002 |
| CN | 1803605 A | 7/2006 |
| CN | 101087579 A | 12/2007 |
| CN | 101205068 A | 6/2008 |
| EP | 1 206 928 A1 | 5/2002 |
| JP | 2006-117646 A | 5/2006 |
| WO | WO 2008/071466 A1 | 6/2008 |
| WO | WO 2010/100350 A2 | 9/2010 |

OTHER PUBLICATIONS

International Search Report Issued Apr. 5, 2011 in PCT/EP2010/068324.
Chinese Search Report Issued Mar. 1, 2013 in Patent Application No. 201080059489.X (English translation only).
"Specialty Silica", Evonik Industries, May 2009, pp. 1-36.

* cited by examiner

*Primary Examiner* — Robert A Wax
*Assistant Examiner* — H. Sarah Park
(74) *Attorney, Agent, or Firm* — Oblon, Spivak, McClelland, Maier & Neustadt, L.L.P.

(57) ABSTRACT

A powdery composition, comprising: a) core-shell particles having a shell of hydrophobic or hydrophobized particles; and b) a carrier powder comprising a carrier and at least one of an at least partially water soluble liquid and a water reactive substrate reversibly bound to the carrier by at least one of the capillary action, absorption and adsorption is provided. The core-shell particles have a core, comprising: water; and 0 to 10 wt. % of a total core weight of a dissolved or emulsified material. The carrier comprises at least one material selected from the group consisting of silica, a silica-metal mixed oxide, phyllosilicate, starch, hollow glass spheres, nylon, sugar, cyclodextrines and polysaccharides, and a weight ratio of the carrier powder to the core-shell particles is from 1/1 to 1/9. A creamy composition is manufactured from the powdery composition-by an energy input in form of pressure, shear, temperature, vibration and/or solvent addition, the energy input being sufficient to release the liquid water or the liquid aqueous phase from the core-shell material and subsequently dissolving or flushing the produce or products from the carrier.

9 Claims, No Drawings

WATER CONTAINING POWDER COMPOSITION

FIELD OF THE INVENTION

The invention relates to a water containing powder composition and a process to produce a creamy composition from this powdery composition.

BACKGROUND OF THE INVENTION

Solid cosmetic preparations, such as powders, having a high water content are known in the prior art. The basis of some patent applications is the long-known fact that in the presence of a hydrophobic powder, such as a hydrophobic silicon dioxide powder, water can be dispersed into fine droplets and enveloped by the hydrophobic material, thus preventing the droplets from rejoining. A powdery substance having a high water content, known as "dry water", is formed in this way (Fine Particles series no. 11, Evonik Degussa). Cosmetic formulations based on "dry water" are described in Seifen, Fette, Öle, Wachse (SÖFW), 8 (2003), pages 1-8. These are free-flowing, fine powders, which liquefy when rubbed on the skin. Water-containing, liquefiable powder compositions based on this principle are further disclosed in several patent applications and patents.

U.S. Pat. No. 4,274,883 discloses an aqueous dispersion of a hydrophobic silica consisting of 0.1 to 50 parts of hydrophobic silica, in a given case up to 3 parts of wetting agent and 99.9 to 50 parts of water. It is produced by intensive mixing of hydrophobic silica with water with the known "dry-water-phase" as an intermediate step. In a given case there can additionally be used a wetting agent in which case the "dry-water-phase" does not occur. The dispersion of hydrophobic silicas can be mixed without additional steps or materials with rubber latex.

DE-A-1467023 discloses the use of aqueous solutions comprising cosmetic ingredients instead of pure water for the preparation of dry water.

EP-A-1206928 discloses a water-containing powder composition comprising aqueous gel cores coated with hydrophobic particles.

JP 2000-309505 discloses a cosmetic powder being liquefied by embrocation including 2-20 wt. % of a hydrophobic silica having a specific surface area of at least 60 m2/g and an oil-in-water type emulsion composition.

EP-A-1235554 discloses a cosmetic or pharmaceutical powder-to-liquid composition comprising hydrophobically coated silica particles into which are incorporated water and a water soluble polymer, the composition containing less than 1% oil.

EP-A-1386599 discloses a method for producing dry water composed of an aqueous ingredient coated with a hydrophobic powder to form a powder state capable of liquefying upon embrocation at the time of use, comprising charging a hydrophobic powder and an aqueous ingredient into a hollow container forming a hydrophobic enclosed space in the inside thereof, followed by agitating at a high speed in the hydrophobic hollow container to form fine aqueous droplets, and then allowing the surface of the fine aqueous droplets to be uniformly adsorbed with the hydrophobic powder.

WO 01/85138 A2 discloses an encapsulation system comprising a core of aqueous liquid having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the encapsulated particles are spherical and can support its own weight.

EP-A-855177 discloses a whitening powder comprising 0.1 to 7 wt. % trimethylsiloxylated silica having a specific surface area of at least 80 $m^2/g$ and a hydrophobicization degree of at least 50%, 5 to 40 wt. % of a polyhydric alcohol, 50 to 94 wt. % water and 0.01 to 5 wt. % of a whitening ingredient.

WO 2005/058256 discloses cosmetic preparations of creme- or paste-like consistency, comprising 50-95 wt. % water, hydrophobized silicon dioxide powder, at least one cosmetically-relevant active ingredient, or adjunct which is water soluble or which may be dispersed or emulsified in an aqueous medium and a viscosity regulator. The above is produced by continuously adding hydrophobized silicon dioxide powder with mixing, to a solution or a dispersion of at least one cosmetically-relevant active ingredient and the mixing is continued until a paste-like consistency is achieved.

Although prior art includes concepts such as the encapsulation of water, the problem with this concept is the amount of additives that could be added while maintaining a stable powder ranged from 0 to 3% by weight depending on additive properties such as the polarity and chain length of the additives. Limiting the formulation to 0 to 3% by weight of an additive, and limiting the additives, reduced the feasibility of the original concept. Even with guidance the industries that have tried using this concept had been unable to overcome the limitations regarding the variety of additives or additive amount.

DETAILED DESCRIPTION OF THE INVENTION

It is therefore an object of the present invention to provide a concept that overcomes past difficulties. The concept should not be restricted to cosmetic purposes, but should also allow introduction into other industries like personal care or household care.

The present invention provides a powdery composition comprising
a) at least one powder in form of core-shell particles, the core comprising liquid water or a liquid aqueous phase and the shell comprising hydrophobic or hydrophobized particles and
b) at least one powder comprising a carrier and
b1) a at least partially water soluble liquid and/or
b2) a water reactive substrate
each located in and/or on the carrier.

The water soluble liquid and the water reactive substrate are reversibly bound to the carrier by capillary action/absorption/adsorption and can be flushed or dissolved from the carrier, in part or completely, by the liquid water or the liquid aqueous phase of the core-shell particles. The carrier itself can be water soluble or not.

The core shell particles as part of the composition according to the invention refer to a powdered material, that contains liquid water or a liquid aqueous phase, but where the coalescence of the individual water droplets is prevented by a shell of hydrophobic or hydrophobized particles. The shell is able to release the liquid aqueous phase or liquid water from the core when activated by pressure, shear, temperature, vibration and/or addition of one or more solvents or one or more surfactants. These kind of core shell particles are known as "dry water". The aqueous phase may be an aqueous solution, an aqueous dispersion or an aqueous emulsion.

Hydrophobic particles are understood to be hydrophobic particles per se, whereas hydrophobized particles are those obtained by reacting the surface of a hydrophilic particle with a hydrophobic surface modifying agent. Usually a covalent bond is formed between reactive groups at the surface of the particles, e.g. hydroxyl groups, and reactive groups of the surface modifying agent.

In general "hydrophobic" means that there is only a small or no interaction with water and the affinity with water is small or zero. A methanol wettability may be used as a quantitative measure of the hydrophobicity. The shell particles of the present invention should have a methanol wettability of at least 40, preferably 50 to 80, more preferably 60 to 70. For the determination of the methanol wettability, in each case 0.2 g (±0.005 g) of hydrophobic or hydrophobized particles are weighed into transparent centrifuge tubes. 8.0 ml portions of a methanol/water mixture with 10, 20, 30, 40, 50, 60, 70 or 80 vol. % methanol are added to each sample. The tubes are shaken for 30 seconds and then centrifuged at 2500 min$^{-1}$ for 5 minutes. The methanol wettability is the defined as the volume per cent of methanol for which the sediment volume is 100%. The higher the number the higher the hydrophobicity.

The hydrophobic or hydrophobized shell of the core shell particles usable in the present invention comprise for example inorganic powders such as talc, kaolin, mica, sericite, dolomite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, tungstenic acid metal salts, magnesium, silica, zeolite, barium sulfate, calcined calcium sulfate, calcium phosphate, fluorapatite, hydroxyapatite, titania, fumed titania, alumina and fumed alumina.

Among these hydrophobized silica particles which form a three dimensional network, an aggregated structure, are a preferred shell material. The silica may be a precipitated silica or a fumed silica, the latter being preferred. Fumed silica is obtained in a flame hydrolysis or flame oxidation process. Its purity is higher than 99 wt.-%, usually higher than 99.8 wt.-%. Fumed silica usually forms a three-dimensional network of aggregated primary particles. The fumed silica primary particles bear hydroxyl groups at their surface and are nonporous.

Precipitated and fumed silica particles, as well as other particles suitable as shell particles are hydrophilic particles which need to be hydrophobized in a subsequent step. Procedures for this step are known for the person skilled in the art.

Suitable surface modifying agents can be the following silanes, which may be used individually or as a mixture.

Organosilanes $(RO)_3Si(C_nH_{2n+1})$ and $(RO)_3Si(C_nH_{2n-1})$ with R=alkyl, such as methyl, ethyl, n-propyl, isopropyl, butyl and n=1–20.

Organosilanes $R'_x(RO)_ySi(C_nH_{2n+1})$ and $R'_x(RO)_ySi(C_nH_{2n-1})$ with R=alkyl, such as methyl, ethyl, n-propyl, isopropyl, butyl; R'=alkyl, such as methyl, ethyl, n-propyl, isopropyl, butyl; R'=cycloalkyl; n=1–20; x+y=3, x=1, 2; y=1, 2.

Haloorganosilanes $X_3Si(C_nH_{2n+1})$ and $X_3Si(C_nH_{2n-1})$ with X=Cl, Br; n=1–20. Haloorganosilanes $X_2(R')Si(C_nH_{2n+1})$ and $X_2(R')Si(C_nH_{2n-1})$ with X=Cl, Br, R'=alkyl, such as methyl, ethyl, n-propyl, isopropyl, butyl-; R'=cycloalkyl; n=1–20.

Haloorganosilanes $X(R')_2Si(C_nH_{2n+1})$ and $X(R')_2Si(C_nH_{2n-1})$ with X=Cl, Br; R'=alkyl, such as methyl-, ethyl-, n-propyl-, isopropyl-, butyl-; R'=cycloalkyl; n=1–20.

Organosilanes $(RO)_3Si(CH_2)_m$—R' with R=alkyl, such as methyl-, ethyl-, propyl-; m=0-20, R'=methyl, aryl such as —$C_6H_5$, substituted phenyl radicals, $C_4F_9$, $OCF_2$—CHF—$CF_3$, $C_6F_{13}$, $OCF_2CHF_2$, $S_x$—$(CH_2)_3Si(OR)_3$.

Organosilanes $(R'')_x(RO)_ySi(CH_2)_m$—R' with R''=alkyl, x+y=3; cycloalkyl, x=1, 2, y=1, 2; m=0.1-20; R'=methyl, aryl, such as $C_6H_5$, substituted phenyl radicals, $C_4F_9$, $OCF_2$—CHF—$CF_3$, $C_6F_{13}$, $OCF_2CHF_2$, $S_x$—$(CH_2)_3Si(OR)_3$, SH, NR'R''R''' with R'=alkyl, aryl; R''=H, alkyl, aryl; R'''=H, alkyl, aryl, benzyl, $C_2H_4NR''''R'''''$ with R''''=H, alkyl and R'''''=H, alkyl.

Haloorganosilanes $X_3Si(CH_2)_m$—R' with X=Cl, Br; m=0-20; R'=methyl, aryl such as $C_6H_5$, substituted phenyl radicals, $C_4F_9$, $OCF_2$—CHF—$CF_3$, $C_6F_{13}$, O—$CF_2$—$CHF_2$, $S_x$—$(CH_2)_3Si(OR)_3$, where R=methyl, ethyl, propyl, butyl and x=1 or 2, SH.

Haloorganosilanes $RX_2Si(CH_2)_mR'$ with X=Cl, Br; m=0-20; R'=methyl, aryl such as $C_6H_5$, substituted phenyl radicals, $C_4F_9$, $OCF_2$—CHF—$CF_3$, $C_6F_{13}$, O—$CF_2$—$CHF_2$, —OOC$(CH_3)C$=$CH_2$, —$S_x$—$(CH_2)_3Si(OR)_3$, where R=methyl, ethyl, propyl, butyl and x=1 or 2, SH.

Haloorganosilanes $R_2XSi(CH_2)_mR'$ with X=Cl, Br; m=0-20; R'=methyl, aryl such as $C_6H_5$, substituted phenyl radicals, $C_4F_9$, $OCF_2$—CHF—$CF_3$, $C_6F_{13}$, O—$CF_2$—$CHF_2$, —$S_x$—$(CH_2)_3Si(OR)_3$, where R=methyl, ethyl, propyl, butyl and x=1 or 2, SH.

Silazanes $R'R_2SiNHSiR_2R'$ with R,R'=alkyl, vinyl, aryl.

Cyclic polysiloxanes D3, D4, D5 and their homologs, with D3, D4 and D5 meaning cyclic polysiloxanes having 3, 4 or 5 units of the type —O—Si(CH$_3$)$_2$, e.g. octamethylcyclotetrasiloxane=D4.

Polysiloxanes or silicone oils of the type Y—O[[—SiRR'—O]$_m$—[SiR''R'''—O]$_n$]$_u$—Y with R=alkyl; R'=alkyl, aryl, H; R''=alkyl, aryl; R'''=alkyl, aryl, H; Y=$CH_3$, H, $C_zH_{2z+1}$ with z=1-20, Si(CH$_3$)$_3$, Si(CH$_3$)$_2$H, Si(CH$_3$)$_2$OH, H, Si(CH$_3$)$_2$(OCH$_3$), Si(CH$_3$)$_2$(C$_z$H$_{2z+1}$) and z=1-20, m=0, 1, 2, 3, . . . , n=0, 1, 2, 3, . . . , u=0, 1, 2, 3, . . . .

As surface modifying agents the following compounds may be preferred: octyltrimethoxysilane, octyltriethoxysilane, hexamethyldisilazane, hexadecyltrimethoxysilane, hexadecyltriethoxysilane, dimethylpolysiloxane, nonafluorohexyltrimethoxysilane, tridecafluorooctyltrimethoxysilane, tridecafluorooctyltriethoxysilane. With particular preference it is possible to use hexamethyldisilazane, octyltriethoxysilane and dimethyl polysiloxanes.

The shell particles of the powdery composition according to the invention can be hydrophobized silica particles having a BET surface area preferably from 30 m$^2$/g to 500 m$^2$/g, more preferably of 100 m$^2$/g to 350 m$^2$/g. Due to the reaction with the surface modifying agent these particles may contain 0.1 to 15 wt.-%, usually 0.5. to 5 wt.-%, of carbon.

Typical examples that may be used as shell material are AEROSIL® R104 (octamethylcyclotetrasiloxane; 150 m$^2$/g; 55); AEROSIL® R106 (octamethylcyclotetrasiloxane; 250 m$^2$/g; 50), AEROSIL® R202 (polydimethylsiloxane; 100 m$^2$/g; 75), AEROSIL® R805 (octylsilane; 150 m$^2$/g; 60), AEROSIL® R812 (hexamethyldisilazane; 260 m$^2$/g; 60), AEROSIL® R812S (hexamethyldisilazane; 220 m$^2$/g; 65), AEROSIL® R8200 (hexamethyldisilazane; 150 m$^2$/g; 65).

The indication in parenthesis refer to the surface modifying agent, the approximate BET surface area and the approximate methanol wettability, determined by the procedure given in this specification.

Particularly useful shell particles material are hydrophobized silica particles which are obtained by reacting a hydrophilic fumed silica particles having a BET surface area of from 270 to 330 m$^2$/g with hexamethyldisilazane. The obtained hydrophobized silica particles have a BET surface area of from 200 to 290 m$^2$/g, a carbon content of 2 to 4 wt.-% and a methanol wettability of at least 50, more preferred 50 to 70.

It may also be beneficial to use hydrophobized fumed silica particles in compacted form or as granules.

The other part of the core shell particles to be discussed is the core. The core contains liquid water, either in form of liquid water itself, or as a liquid aqueous solution, an emulsion containing liquid water or as an aqueous dispersion. The dissolved or emulsified material in case of a liquid aqueous solution or emulsion or the solid material in case of an aqueous dispersion should be selected from those materials that neither significantly reduce the surface tension of the core nor cause wetting of the hydrophobic or hydrophobized particles of the shell. For the liquid aqueous solution this means that the solution should not contain more than 10 wt.-%, preferable not more than 3 wt.-%, of dissolved material. Liquid water itself is the most preferred core material.

The core can consist of a liquid aqueous phase containing up to 10 wt.-% of compounds typically be used in the fields of cosmetic, personal care or household care may be used, as long as they do not reduce the surface tension of the core nor cause wetting of the hydrophobic or hydrophobized particles of the shell. Typical example will be discussed together with the carrier containing a at least partially water soluble liquid and/or a water reactive substrate.

The water content of the core-shell particles usually is in a range from 75 to 95 wt.-%, based on the core shell particle.

The powdery composition according to the invention consists of a powder next to the core shell particles that consists of at least one other powder, defined as a carrier containing a at least partially water soluble liquid or a water reactive substrate, each located in and/or on a carrier.

The water soluble liquid is capable of being flushed or dissolved from the carrier, in part or completely, by the core material of the core-shell particles in case the core shell particles are activated by pressure, shear, temperature, vibration and/or addition of one or more solvents or one or more surfactants. This means that the water soluble liquid is either partially or completely dissolved from carrier by the water or the aqueous phase of the core. Or the water soluble liquid can be flushed, partially or completely, form carrier by the water or the aqueous phase of the core.

The same applies for a water reactive substrate. A water reactive substrate is a material which is not water soluble or soluble only to a small amount. When being activated by water or an aqueous phase it is transformed to a reaction product or products that are essentially or completely water soluble.

The carrier is preferably selected from the group consisting of silica, silica-metal mixed oxides, like silica-alumina mixed oxides, silica-titania mixed oxides, phyllosilicate, starch, hollow glass spheres, nylon, sugar, cyclodextrines and polysaccharides.

In a special embodiment of the invention the carrier is selected from fumed silica or precipitated silica, good results being obtained with hydrophilic as well as hydrophobized forms.

In another special embodiment of the invention the carrier is a precipitated silica having
   a) a BET surface area from 50 to 1000 m$^2$/g, preferably from 100 to 700 m$^2$/g, more preferably 150 to 500 m$^2$/g,
   b) a particle size d$_{50}$, determined by laser diffraction, from 2 to 100 µm, preferably 3 to 20 µm, more preferably 4 to 10 µm and
   c) a DBP (dibutyl phthalate) absorption, in g DBP/100 g silica, of from 200 to 400, preferably 250 to 350.

The BET surface area is determined according to ISO 5794-1, annex D, the particle size d$_{50}$ is determined according to ASTM 690-1992, and the DBP absorption is determined according to ASTM D 2414, based on the substance after drying.

Special grades of precipitated silica comprise a material having a BET surface area of from 400 to 500 m$^2$/g, a particle size d$_{50}$ of 4 to 6 µm and a DBP absorption of 300 to 350 g DBP/100 g silica. Also another material having a BET surface area of from 150 to 250 m$^2$/g, a particle size d$_{50}$ of 4 to 7 µm and a DBP absorption of 250 to 300 g DBP/100 g silica. Typical examples are SIPERNAT® 500 LS and SIPERNAT® 22 LS, both from Evonik Degussa.

The weight ratio of the at least partially water soluble liquid and/or water reactive substrate to carrier is determined by multiple factors such as the viscosity of the water soluble liquid, the structure of carrier comprising the pore size, the pore volume and the BET surface area. Usually is in the range of 10 to 90, a range from 60 to 75 being preferred.

The weight ratio of the carrier including the at least partially water soluble liquid and/or water reactive substrate to the core-shell particles usually is from 1:1 to 1:9.

The average particle size of the carrier and of the core-shell particles, determined for example by transmission electron microscopy, usually can vary, independently from each other, from 2 to 20 µm. An average particle size of the core shell particles of 50 to 150% of the average particles size of the carrier may be preferred.

The aqueous phase of the core of the core-shell particles and/or the at least partially water soluble liquid and/or water reactive substrate, each in and/or on the carrier comprises at least one of the materials of the group consisting of comprises at least one of the materials of the group consisting of UV light protection filters, antioxidants, moisturizing substances, deodorant, antiperspirant active compounds, biogenic substances, insect repellent active compounds, bleaching agents antioxidant, bleach, antibacterial substances, antifungal substances, flavors, fragrances, acids, alkalis, enzymes or mixtures thereof.

UV light protection filters, according to the invention, are organic substances which are liquid or crystalline at room temperature and are capable of absorbing ultraviolet rays and of releasing the absorbed energy again in the form of radiation of longer wavelength, for example heat. UV filters can be oil-soluble or water-soluble. Oil-soluble substances are for example:
   3-benzylidenecamphor and 3-benzylidenenorcamphor and derivatives thereof,
   4-aminobenzoic acid derivatives, preferably 4-(dimethylamino)benzoic acid 2-ethylhexyl ester, 4-(dimethylamino)benzoic acid 2-octyl ester and 4-(dimethylamino)benzoic acid amyl ester- esters of cinnamic acid, preferably 4-methoxycinnamic acid 2-ethylhexyl ester, 4-methoxycinnamic acid propyl ester, 4-methoxycinnamic acid isoamyl ester, 2-cyano-3,3-phenylcinnamic acid 2-ethylhexyl ester (octocrylene)
   esters of salicylic acid, preferably salicylic acid 2-ethylhexyl ester, salicylic acid 4-isopropylbenzyl ester, salicylic acid homomenthyl ester
   derivatives of benzophenone, preferably 2-hydroxy-4-methoxybenzophenone, 2-hydroxy-4-methoxy-4'-methylbenzophenone, 2,2'-dihydroxy-4-methoxybenzophenone
   esters of benzalmalonic acid, preferably 4-methoxybenzalmalonic acid di-2-ethylhexyl ester triazine derivatives, such as 2,4,6-trianilino-(p-carbo-2'-ethyl-1'-hexyloxy)-1,3,5-triazine, octyl triazone and dioctyl butamido triazone propane-1,3-diones, such as 1-(4-tert-butylphenyl)-3-(4'-methoxyphenyl)propane-1,3-dione Possible water-soluble substances are:

2-phenylbenzimidazole-5-sulfonic acid and alkali metal, alkaline earth metal, ammonium, alkylammonium, alkanolammonium and glucammonium salts thereof sulfonic acid derivatives of benzophenones, preferably 2-hydroxy-4-methoxybenzophenone-5-sulfonic acid and its salts sulfonic acid derivatives of 3-benzylidenecamphor, such as, for example, 4-(2-oxo-3-bornylidenemethyl)benzenesulfonic acid and 2-methyl-5-(2-oxo-3-bornylidene) sulfonic acid and salts thereof.

Typical UV-A filters are derivatives of benzoylmethane, such as 1-(4'-tert-butylphenyl)-3-(4'-methoxyphenyl)propane-1,3-dione, 4-tert-butyl-4'-methoxydibenzoylmethane, 1-phenyl-3-(4'-isopropylphenyl)-propane-1,3-dione.

The UV-A and UV-B filters can of course also be employed in mixtures. Particularly favourable combinations comprise the derivatives of benzoylmethane, for example 4-tert-butyl-4'-methoxydibenzoylmethane and 2-cyano-3,3-phenylcinnamic acid 2-ethyl-hexyl ester (octocrylene) in combination with esters of cinnamic acid, preferably 4-methoxycinnamic acid 2-ethylhexyl ester and/or 4-methoxycinnamic acid propyl ester and/or 4-methoxycinnamic acid isoamyl ester. Such combinations are advantageously combined with water-soluble filters, such as, for example, 2-phenylbenzimidazole-5-sulfonic acid and alkali metal, alkaline earth metal, ammonium, alkylammonium, alkanolammonium and glucammonium salts thereof.

In addition to the organic substances mentioned, insoluble light protection pigments, namely finely disperse metal oxide powders, as such or in hydrophobized form, and salts are also possible for this purpose. Examples of suitable metal oxide powders or hydrophobized metal oxide powders can be titanium dioxide powder, zinc oxide powder and/or a mixed oxide powder of these with the elements Si, Ti, Al, Zn, Fe, B, Zr and/or Ce.

Typical examples are coated titanium dioxides, such as UV-Titan M212, M 262 and X 111 (Kemira), AEROXIDE® TiO2 P25, PF2, T 805 and T 817 (Evonik Degussa), Micro Titanium Dioxide MT-150 W, MT-100 AQ, MT-100 SA, MT-100 HD, MT-100 TV (Tayca), Eusolex® T2000 (Merck), Zinc Oxide neutral H&R and Zinc Oxide NDM (Haarmann & Reimer) as well as Z-Cote and Z-Cote HP1 (BASF).

Dispersions, such as, for example, TEGO Sun TAQ 40, a 40 wt. % strength aqueous dispersion of a hydrophobized titanium dioxide (Evonik Goldschmidt) can also be used.

Typical antioxidants as part of the powdery composition according to the invention can be amino acids like glycine, histidine, tyrosine or tryptophan and derivatives thereof, imidazoles like urocanic acid) and derivatives thereof, peptides, such as D,L-carnosine, D-carnosine, L-carnosine and derivatives thereof, carotenoids, carotenes, alpha-carotene, beta-carotene, lycopene and derivatives thereof, chlorogenic acid and derivatives thereof, liponic acid and derivatives thereof chelators like alpha-hydroxy-fatty acids, palmitic acid, phytic acid, alpha-hydroxy acids like citric acid, lactic acid, malic acid unsaturated fatty acids and derivatives thereof, like gamma-linolenic acid, linoleic acid, oleic acid, folic acid and derivatives thereof, ubiquinone and ubiquinol and derivatives thereof, vitamin C and derivatives like ascorbyl palmitate, ascorbyl phosphate, ascorbyl acetate, tocopherols and derivatives like vitamin E, vitamin E acetate, vitamin A and derivatives like vitamin A palmitate mannose and derivatives thereof, superoxide dismutase.

Moisturising substance may be selected from the group consisting of ethylene glycol, butylene glycol, 2,3-butandiol, propylene glycol, dipropylene glycol, tripropylene glycol, hexylene glycol, glycerine, diglycerine, glucose, fructose, lactose, saccharose, maltose, mannitol, mannose, PEG-4 to PEG-800, like PEG-4, PEG-6, PEG-7, PEG-8, PEG-9, PEG-10, PEG-12, PEG-14, PEG-16, PEG-18, PEG-20, sorbitol, polyglyceryl sorbitol, urea, xylitol and mixtures thereof.

The deodorant and antiperspirant active compounds can be at least one selected from the group consisting of astringent metal salts, such as aluminium hydrochlorides, aluminium hydroxylactates, aluminium zirconium hydrochlorides and zinc salts germ-inhibiting agents, such as chitosan, phenoxyethanol, chlorhexidine gluconate or 5-chloro-2-(2,4-dichlorophenoxy)-phenol enzyme inhibitors, such as i) trialkyl citrates, such as trimethyl citrate, tripropyl citrate, triisopropyl citrate, tributyl citrate and triethyl citrate;

ii) sterol sulfates or phosphates, such as lanosterol, cholesterol, campesterol, stigmasterol and sitosterol sulfate and phosphate, iii) dicarboxylic acids and esters thereof, such as, for example, glutaric acid, glutaric acid monoethyl ester, glutaric acid diethyl ester, adipic acid, adipic acid monoethyl ester, adipic acid diethyl ester, malonic acid and malonic acid diethyl ester, iv) hydroxycarboxylic acids and esters thereof, such as, for example, citric acid, malic acid, tartaric acid or tartaric acid diethyl ester; or v) 4-hydroxybenzoic acid and its salts and esters, N-(4-chlorophenyl)-N'-(3,4-dichlropheny)urea, 2,4,4'-trichloro-2'-hydroxy-diphenyl ether (Triclosan), 4-chloro-3,5-dimethyl-phenol, 2,2'-methylene-bis(6-bromo-4-chlorophenol), 3-methyl-4-(1-methylethyl)-phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide thymol, thyme oil, eugenol, clove oil, menthol, mint oil, farnesol, phenoxyethanol, glycerol monocaproate, glycerol monocaprylate, glycerol monolaurate, diglycerol monocaproate (DMC), salicylic acid N-alkylamides, such as salicylic acid n-octylamide or salicylic acid n-decylamide.

absorbers or odour maskers like benzyl acetate, p-tert-butylcyclohexyl acetate, linalyl acetate, phenylethyl acetate, linalyl benzoate, benzyl formate, allylcyclohexyl propionate, styrallyl propionate and benzyl salicylate, benzyl ethyl ether, citral, citronellal, citronellyloxyacetaldehyde, cyclamenaldehyde, hydroxycitronellal, jonones, methyl cedryl ketone, anethole, citronellol, eugenol, isoeugenol, geraniol, linalool, phenylethyl alcohol, terpineol or terpenes.

The biogenic substances may be selected from at least one of the group consisting of tocopherol, tocopherol acetate, tocopherol palmitate, ascorbic acid, (deoxy)ribonucleic acid and fragmentation products thereof, beta-glucans, retinol, bisabolol, allantoin, phytantriol, panthenol, pantothenic acid, fruit acids, alpha-hydroxy acids, amino acids, ceramides, pseudoceramides, essential oils, plant extracts, such as, for example, prunus extract, bambara nut extract and vitamin complexes.

The insect repellent active compounds may be selected from the group consisting of N,N-diethyl-m-toluamide, 1,2-pentanediol, 3-(N-n-butyl-N-acetyl-amino)-propionic acid ethyl ester and butyl acetylaminopropionate.

Examples of bleaching agents suitable for the present invention are hydroquinone, zinc peroxide, urea peroxide, hydrogen peroxide and/or organic peroxides.

In a special embodiment of the invention the core of the core-shell particles is water, and the shell consists of hydrophobized fumed silica particles that are obtained by reacting a hydrophilic fumed silica having a BET surface area of from 30 to 500 $m^2/g$.

Furthermore in an advantageous embodiment of the invention the hydrophobized fumed silica particles are obtained by reacting a hydrophilic fumed silica having a BET surface area from 270 to 330 $m^2/g$ with hexamethyldisilazane to give hydrophobized fumed silica particles having a BET surface area of from 200 to 290 $m^2/g$ and a carbon content of 2 to 4 wt.-% and methanol wettability of at least 50.

The special embodiment may further comprise as carrier a precipitated silica having a BET surface area from 400 to 500 $m^2/g$, a particle size $d_{50}$, determined by laser diffraction, from 4 to 6 μm and a DBP (dibutyl phthalate) absorption, in g DBP/100 g silica, from 300 to 350.

The special embodiment may also further comprise as carrier a precipitated silica having a BET surface area from 150 to 250 $m^2/g$, a particle size $d_{50}$, determined by laser diffraction, from 4 to 7 μm and a DBP (dibutyl phthalate) absorption, in g DBP/100 g silica, from 250 to 300.

In addition the special embodiments may further comprise as at least partially water soluble liquid and/or water reactive substrate, each located in and/or on the carrier, and UV light protection filters, antioxidants, moisturizing substances, deodorant, antiperspirant active compounds, biogenic substances, insect repellent active compounds, bleaching agents antioxidant, bleach, antibacterial substances, antifungal substances, flavors, fragrances, acids, alkalis, enzymes or mixtures thereof.

Another object of the invention is a process for the manufacture of a creamy composition, starting form the powdery composition according to the invention. This powdery composition is activated by an energy input in form of pressure, shear, temperature, vibration and/or solvent addition, the energy input being sufficient to release the liquid water or the liquid aqueous phase from the core-shell material, the liquid water or the liquid aqueous phase subsequently is
  a) dissolving or flushing the at least partially water soluble liquid from the carrier and/or
  b) activating the water reactive substrate in and/or on the carrier and subsequently dissolving or flushing the product or products obtained by activating from the carrier.

"Creamy" is understood to mean a range from more liquid compositions to more gel like compositions to creamy compositions.

Having generally described this invention, a further understanding can be obtained by reference to certain specific examples which are provided for illustration only, and are not intended to be limiting.

EXAMPLES

Example 1

Powder-to-Cream-to-Powder Foundation according to the State-of the-Art Way

To create the dry water formulation, 77.5 wt.-% of deionized (DI) water was added to the KitchenAid blender model #KSB5ER4 along with 10.48 wt.-% Carbowax Sentry® Polyethylene Glycol 400 NF from The Dow Chemical Company, 5.27 wt.-% Dimethisil® DM-20 (20cPs) from Chemsil Silicones, Inc., 1.75 wt.-% iron oxide pigments, AC-5 Red R516P, AC-5 Yellow LL-100P, AC-5 Black BL-100P, and AC-5 TiO2 CR-50, from Kobo. AEROSIL® R812S was added at 5.0 wt.-% on top of the water/PEG/Dimethicone/Pigments mixture. The lid was placed tightly on the blender and the mixture was blended at the highest setting (Liquefy) at 9,700 RPM for one minute. During the one minute of mixing, the entire blender was tilted at a 50-60 degree angle from left to right with 10 second hold times.

The product is a cream/mousse texture that has a clear separation on the bottom after about 30 minutes. The process of adding the PEG and Dimethicone failed since no stable discreet droplet was formed when blended together with the hydrophobic silica. It is believed that the emollients lowered the surface tension of water so much that it was able to overcome the interfacial tension between droplets and the AEROSIL® R812S.

Example 2

Powder-to-Cream-to-Powder Foundation according to the Invention

To make novel Powder-to-Cream Foundation formulation according to the invention, a PEG/Dimethicone/pigment/DI water dilution was created by mixing 42.9 wt.-% PEG Sentry® Polyethylene Glycol 400 NF from The Dow Chemical Company, 21.4 wt.-% Dimethisil® DM-20 (20cPs) from Chemsil Silicones, 28.6 wt.-% deionized (DI) water, and 7.1 wt.-% AC-5 iron oxide pigments from Kobo. This solution was then added to SIPERNAT® 22LS in 3-4 addition steps using low shear mixing by hand using a metal spatula. The powder product resulted in a mix that consisted of 70 wt.-% emollient/pigment solution, the liquid, and 30 wt-%, the carrier. This powder product will now be referred to as liquid/Carrier.

The dry water was produced by adding 5 wt.-% of AEROSIL® R812S, 20 wt.-% iron oxide AC-5 pigments and 75 wt.-% DI water. The lid was placed tightly on the blender and the mixture was blended at the highest setting (Liquefy) at 9,700 RPM for one minute. During the one minute of mixing, the entire blender was tilted at a 50-60 degree angle from left to right with about 10 second hold times.

Thirty five percent by weight of the liquid/carrier was then gently mixed (tumbled, tossed or folded in) with 65 wt. % of dry water mixture to make the final powder to cream foundation.

This powder was then stored in a plastic container. The powdery composition was able to be created, and stay, as a powder Example 3

Powder-to-Cream Vitamin Rub according to the State-of-the-Art Way 13.71 wt.-% emollient, polyethylene glycol (PEG Sentry® Polyethylene Glycol 400 NF from The Dow Chemical Company), 2.75 wt.-% Vitamin E (JEEN International Corp.), 78.54 wt.-% DI water and 5.0 wt.-% AEROSIL® R812S were weighed and placed into a KitchenAid blender Model No. KSB5ER4 and blended at its highest speed (9,700 rpm, Liquefy) for 1 minute. During the 1 minute of mixing, the blender was tilted to a 45 degree angle from left to right with hold time of about 10 seconds each side.

The end product was a cream/mousse texture that has a clear separation on the bottom after about half an hour.

The process of adding the emollient and vitamin failed since no stable discreet droplet was formed when blended together with the hydrophobic silica. It is believed that the emollient and vitamin lowered the surface tension of water so much that it was able to overcome the interfacial tension between droplets and the AEROSIL® R812S.

Example 4

Powder-to-Cream Vitamin Rub according to the Invention

A liquid mix of 71.4 wt.-% of polyethylene glycol (PEG Sentry® Polyethylene Glycol 400 NF from The Dow Chemical Company), 14.3 wt.-% Vitamin E (from JEEN International Corp.) and 14.3 wt.-% DI water was made. The liquid mix was then used to make a 64.0 wt.-% liquid mix, to 36.0 wt.-% SIPERNAT® 22LS as carrier. The liquid mix was slowly added to SIPERNAT® 22 LS in 3-4 addition steps, using low shear mixing (in this case, by hand) until the mix was uniform.

The powder obtained (30 wt.-%) was then gently mixed (tumbled, tossed or folded in) to 70 wt.-% dry water.

The powder was then stored in a plastic container.

TABLE 1

Ingredients of the formulations of Examples 1 to 4 [wt.-%]

|  | Ex. 1 | Ex. 2 | Ex. 3 | Ex. 4 |
|---|---|---|---|---|
| Dimethicone | 5.27 | 5.27 | — | — |
| Pigments | 1.75 | 14.75 |  |  |
| Carbowax 400 NF | 10.48 | 10.48 | 13.71 | 13.71 |
| Vitamine E | — | — | 2.75 | 2.75 |
| Deionized Water | 77.50 | 55.75 | 78.54 | 69.24 |
| AEROSIL ® R 812S | 5.00 | 3.25 | 5.00 | 3.50 |
| SIPERNAT ® 22 LS | — | 10.50 | — | 10.80 |

The invention claimed is:

1. A powdery composition, comprising:
a) core-shell particles having a shell of hydrophobized particles; and
b) a carrier powder comprising a carrier and at least one of an at least partially water soluble liquid and/or a water reactive substrate reversibly bound to the carrier by at least one of capillary action, absorption and adsorption; wherein
the core-shell particles have a core, comprising:
water; and
0 to 10 wt. % of a total core weight of a dissolved or emulsified material,
the carrier comprises at least one material selected from the group consisting of silica, a silica-metal mixed oxide, phyllosilicate, starch, hollow glass spheres, nylon, sugar, cyclodextrines and polysaccharides, and
wherein a weight ratio of the carrier including the reversibly bound at least partially water soluble liquid and/or water reactive substrate to the core-shell particles is from 1:1 to 1:9,
wherein
the shell particles comprise hydrophobized silica particles,
a BET surface area of the hydrophobized silica particles is from 200 to 290 m$^2$/g,
a carbon content of the hydrophobized silica particles is 2 to 4 wt.-%,
a methanol wettability of the hydrophobized silica particles is at least 50,
the hydrophobized silica particles are obtained by reacting a hydrophilic fumed silica having a BET surface area of from 270 to 330 m$^2$/g with hexamethyldisilazane,
wherein at least one of
a) the aqueous phase of the core of the core-shell particles and
b) the at least partially water soluble liquid and water reactive substrate comprises at least one material selected from the group consisting of a UV light protection filter, an antioxidant, a moisturizing substance, a deodorant, an antiperspirant active compound, a biogenic substance, an insect repellent active compound, a bleaching agent, an antioxidant, a bleach, an antibacterial substance, an antifungal substance, a flavor, a fragrance, an acid, an alkali, and an enzyme, and
wherein
the carrier is a precipitated silica,
a BET surface area of the precipitated silica is from 400 to 500 m$^2$/g,
a particle size $d_{50}$ of the precipitated silica, determined by laser diffraction, is from 4 to 6 µm, and
a DBP (dibutyl phthalate) absorption of the precipitated silica, in g DBP/100 g silica, is from 300 to 350.

2. The powdery composition according to claim 1, wherein the hydrophobized silica particles are aggregated fumed silica particles.

3. The powdery composition according to claim 1, wherein the core consists of water.

4. The powdery composition according to claim 1, wherein a water content of the core-shell particles is 75 to 95 wt.-%.

5. The powdery composition according to claim 1, wherein an average particle size of the core-shell particles is from 2 to 20 um.

6. The powdery composition according to claim 1, wherein the average particle size of the core shell particles is 50 to 150% of the average particles size of the carrier.

7. A process for the manufacture of a creamy composition, comprising:
activating the powdery composition according to claim 1 by an energy input in form of pressure, shear, temperature, vibration and/or solvent addition,
the energy input being sufficient to release the liquid water or the liquid aqueous phase from the core-shell material,
the liquid water or the liquid aqueous phase subsequently is used for
a) dissolving or flushing the at least partially water soluble liquid from the carrier and/or
b) activating the water reactive substrate in and/or on the carrier and subsequently dissolving or flushing the product or products obtained by activating from the carrier.

8. The powdery composition according to claim 1, wherein the shell particles consist of hydrophobized silica particles.

9. A powdery composition, comprising:
a) core-shell particles having a shell of hydrophobized particles; and
b) a carrier powder comprising a carrier and at least one of an at least partially water soluble liquid and/or a water reactive substrate reversibly bound to the carrier by at least one of capillary action, absorption and adsorption;

wherein
the core-shell particles have a core, comprising:
   water; and
   0 to 10 wt. % of a total core weight of a dissolved or emulsified material,
the carrier comprises at least one material selected from the group consisting of silica, a silica-metal mixed oxide, phyllosilicate, starch, hollow glass spheres, nylon, sugar, cyclodextrines and polysaccharides, and
wherein a weight ratio of the carrier including the reversibly bound at least partially water soluble liquid and/or water reactive substrate to the core-shell particles is from 1:1 to 1:9,
wherein
the shell particles comprise hydrophobized silica particles,
a BET surface area of the hydrophobized silica particles is from 200 to 290 $m^2/g$,
a carbon content of the hydrophobized silica particles is 2 to 4 wt.-%,
a methanol wettability of the hydrophobized silica particles is at least 50,
the hydrophobized silica particles are obtained by reacting a hydrophilic fumed silica having a BET surface area of from 270 to 330 $m^2/g$ with hexamethyldisilazane,
wherein at least one of
a) the aqueous phase of the core of the core-shell particles and
b) the at least partially water soluble liquid and water reactive substrate comprises at least one material selected from the group consisting of a UV light protection filter, an antioxidant, a moisturizing substance, a deodorant, an antiperspirant active compound, a biogenic substance, an insect repellent active compound, a bleaching agent, an antioxidant, a bleach, an antibacterial substance, an antifungal substance, a flavor, a fragrance, an acid, an alkali, and an enzyme, and
wherein
the carrier is a precipitated silica,
a BET surface area of the precipitated silica is from 150 to 250 m2/g,
a particle size $d_{50}$ of the precipitated silica, determined by laser diffraction, is from 4 to 7 um, and
a DBP (dibutyl phthalate) absorption of the precipitated silica, in g DBP/100 g silica, is from 250 to 300.

\* \* \* \* \*